US006656108B1

(12) United States Patent
Spalding, Jr. et al.

(10) Patent No.: US 6,656,108 B1
(45) Date of Patent: Dec. 2, 2003

(54) THERAPEUTIC BALL

(75) Inventors: Robert T. Spalding, Jr., Signal Mountain, TN (US); Dennis Ogrodowczyk, Signal Mountain, TN (US)

(73) Assignee: Les Appel, Cincinnati, OH (US)

( * ) Notice: Subject to any disclaimer, the term of this patent is extended or adjusted under 35 U.S.C. 154(b) by 0 days.

(21) Appl. No.: 10/119,429

(22) Filed: Apr. 9, 2002

Related U.S. Application Data

(60) Provisional application No. 60/282,755, filed on Apr. 10, 2001.

(51) Int. Cl.$^7$ .................................................. A61N 2/00
(52) U.S. Cl. .......................................... 600/9; 606/204
(58) Field of Search ...................... 600/9–15; 607/96, 607/104, 108, 112, 114; 606/204

(56) References Cited

U.S. PATENT DOCUMENTS

| 5,560,746 A | * | 10/1996 | Willow | 601/135 |
| 5,792,176 A | * | 8/1998 | Chang | 606/204 |
| 6,129,659 A | * | 10/2000 | Wilk | 600/9 |
| 6,182,313 B1 | * | 2/2001 | Eschenbach | 5/640 |

* cited by examiner

*Primary Examiner*—John P. Lacyk
(74) *Attorney, Agent, or Firm*—Alan Ruderman; Stephen J. Stark

(57) ABSTRACT

A therapeutic device for treating a portion of a human body has a rigid outer surface with a magnet therein. The outer surface has a curved shape to provide a pressure point proximate to the location of the magnet so that a patient may be simultaneously treated with pressure point therapy and magnetic therapy. Furthermore, the device may be chilled to treat the patient simultaneously with cryotherapy.

13 Claims, 2 Drawing Sheets

THERAPEUTIC BALL

This invention claims the benefit of U.S. Provisional Patent Application No. 60/282,755 filed Apr. 10, 2001.

FIELD OF THE INVENTION

This invention relates to a therapeutic device comprising a shaped structure providing at least one location for applying a pressure point to a part of the human body wherein the application point is proximate to a magnetic field, and more specifically to a rounded urethane ball with a planar surface and a magnet combined therein to provide pressure point therapy, magnetic therapy, and possibly cryotherapy to a part of the body.

BACKGROUND OF THE INVENTION

Magnets have been utilized for therapeutic treatment for a number of years. U.S. Pat. No. 5,950,239 shows magnets utilized in clothing for therapeutic purposes and describes a basic premise of magnetic therapy: subjecting body cells to a low-level magnetic field to assist stressed cells in restoring their correct balance of electrical charge for performing more efficiently.

Numerous pressure point therapy devices are known including such devices as Winger, U.S. Pat. No. 6,201,876 which imparts a pressure point in the form of a curved surface against the body.

Furthermore, various cryotherapy devices including various types of ice bags and ice-packs are available for reducing inflamation are available.

However a need exists to combine the various therapy techniques to take advantage of multiple therapy techniques with a single product, especially one having synegistic virtues.

SUMMARY OF THE INVENTION

A primary object of the invention is to provide a therapeutic device for providing a pressure point to a specific location on the human body while introducing a magnetic field to the area subjected to the pressure point.

Another object of the invention is to provide a therapeutic device which may be reduced in temperature to provide cryotherapy to a specific location while providing at least pressure point therapy, and more preferably, providing both pressure point therapy as well as magnetic therapy.

BRIEF DESCRIPTION OF THE DRAWINGS

The particular features and advantages of the invention as well as other objects will become apparent from the following description taken in connection with the accompanying drawings in which.

DESCRIPTION OF THE PREFERRED EMBODIMENT

Figure 1:
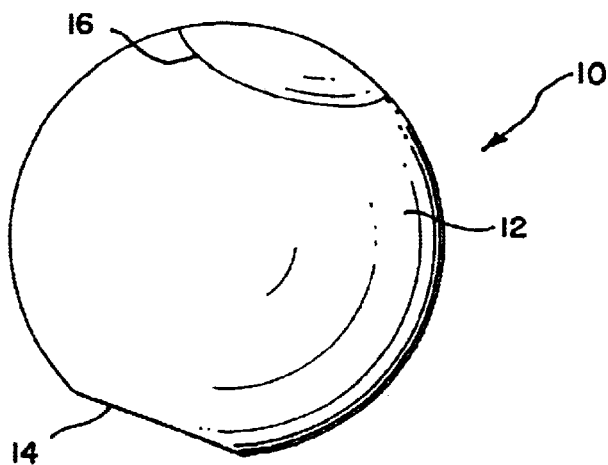
FIG. 1 is a top elevational view of a therapeutic device of the preferred embodiment.
Figure 2:
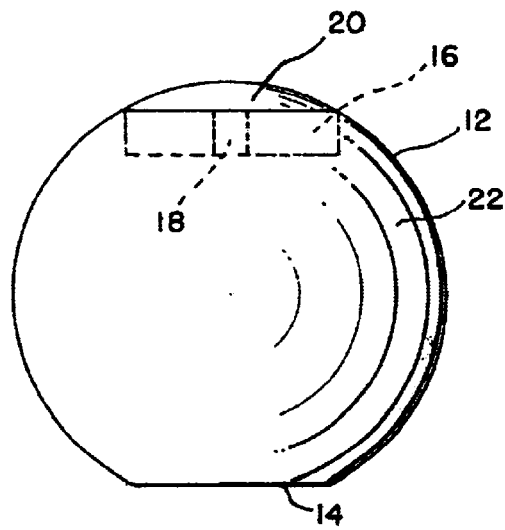
FIG. 2 is a side plan view of the therapeutic device of FIG. 1 with interior portions illustrated in phantom.
Figure 3:
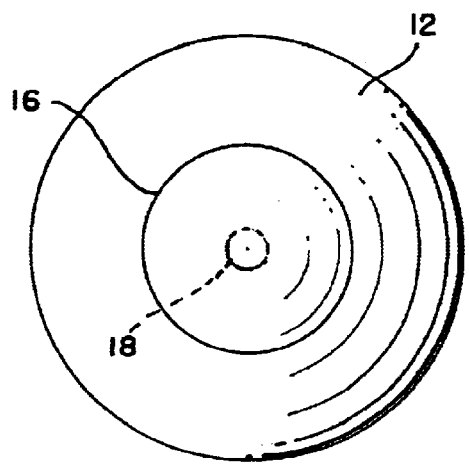
FIG. 3 is a top plan view of the therapeutic device of FIGS. 1 and 2 with interior portions illustrated in phantom.

FIGS. 1–3 show a therapeutic device 10 constructed in accordance with the preferred embodiment of the invention. The device 10 is preferably constructed to provide a rigid outer surface 12 with a planar or flat bottom 14. The flat bottom 14 has been found to assist in maintaining the device 10 in a desired location without it rolling as dictated by gravity when not in use.

The device 10 is preferably fabricated from a two-part urethane resin. A mold may be fashioned from silicone or other appropriate material. A suitable model, such as a table pool ball, or billiard ball, or other suitable shape, may be inserted into liquid silicone. When the silicone cures, the model is removed and a mold remains. Liquid urethane resin may then be poured into the mold.

The two parts of the resin are a polyurethane polymer and a curative. Of course, any of a number of additives could be added to the resin at this time including coloring agents or other components. When the resin is activated by the curative, it is then poured into the mold. A magnet 16 may be placed in the mold first, or it may be placed in the mold at any time during the pouring of the urethane into the mold. Gravity has been found to assist in locating the magnet 16 at the desired location as illustrated in FIGS. 1–3. Only the top edge of the magnet 16 may normally be visible as this is typically where the magnet 16 comes to rest in the mold during the curing process. The resin and mold materials are available from the Synair Corporation of Chattanooga, Tenn. at www.synair.com.

The magnet 16 may be a toroid in shape which allows resin to flow through the center opening 18 in the magnet 16 to the top portion of the mold. With resin connecting the top portion 20 to the bottom portion 22 through the center opening 18 of the magnet 16, there is less of a likelihood that the top portion 20 may be inadvertently sheared off of the device 10 by dropping, etc. However, with a disc, or cylindrical shaped magnet which does not have the center opening 18, there has not been any shearing off problems experienced. The magnet 16 is preferably a ferrite ceramic magnet having about a 1¼ inch outer diameter with a 3/16 inch center opening. The magnet may be about ¼ inch in height. The magnet 16 may be obtained from the Bunting Magnetics Company of Newton, Kans. (www.buntingmagnetics.com). The magnet 16 is located in the top half, and preferably top quarter of the device 10.

Figure 4:
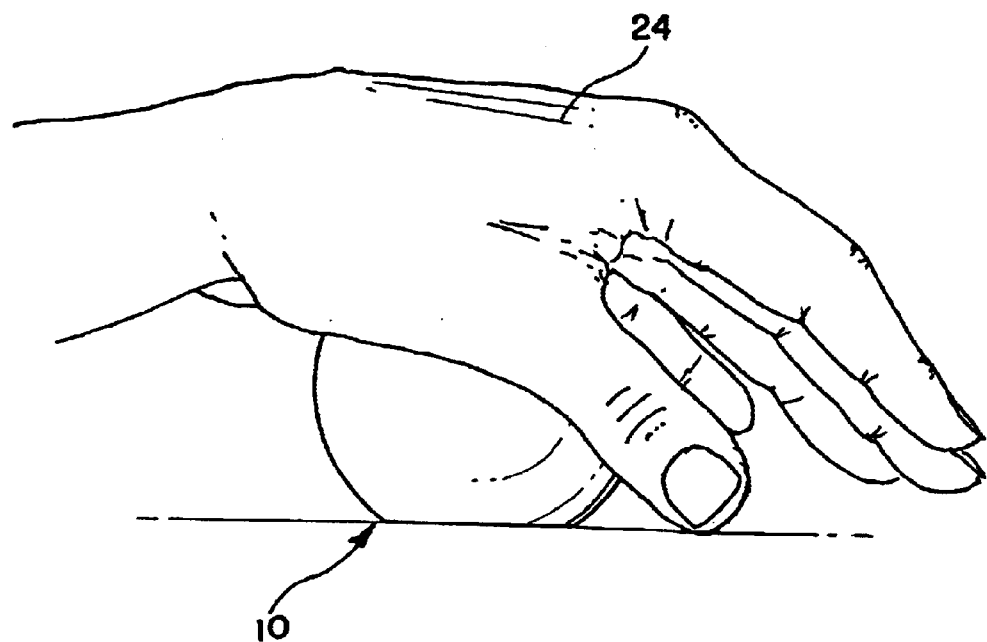
FIG. 4 is a perspective view of an individual utilizing a preferred device to treat carpal tunnel syndrome.

As the resin cures, it becomes hard and creates a solid outer surface 12. The outer surface 12 resists deformation by application of force by a part of a user's body. Accordingly, the outer surface 12, may apply pressure to a specific location on the body of a user. Since the preferred device 10 is ball-shaped or round, there are literally an infinite number of pressure points which may be utilized. The top portion 20 of the ball is the presently preferred pressure point since the flat bottom 14 may be utilized to orient the top 20 as illustrated in FIGS. 2 and 4 on a flat surface.

A user may hold the device 10 to apply pressure to a specific location on the body, or may set the device 10 on a flat surface, such as a table or the floor and allow gravity to at least assist in the application of pressure to a specific location on the body. FIG. 4 shows hand 24 resting atop a preferred device 10. The weight of the hand 24 at rest causes the contact between the surface of the device 10 and the hand 24 to act as a pressure point at that location. The nervovascular bundle in the hand 24 is treated by reflexology of the pressure point therapy and the magnetic therapy induced by the magnet 16. In at least one informal experiment, this process has been found to alleviate some symptoms associated with carpal tunnel syndrome.

In addition to providing a treatment for carpal tunnel syndrome, the device 10 of the preferred embodiment maybe utilized in a similar manner to treat heel arch pain. The device 10 may also be rolled for therapeutic treatment, under the foot, or other appropriate body portion.

Furthermore, the device 10 may be rubbed against body parts such as against the neck. The magnet is believed to provide magnetic therapy in addition to the pressure point therapy delivered by the surface of the device 10. Although the preferred embodiment of the device 10 is substantially round with a flat bottom 14, other embodiments could include a completely round outer surface, or other appropriately curved surfaces, such as parabolic shapes, etc.

Figure 5:
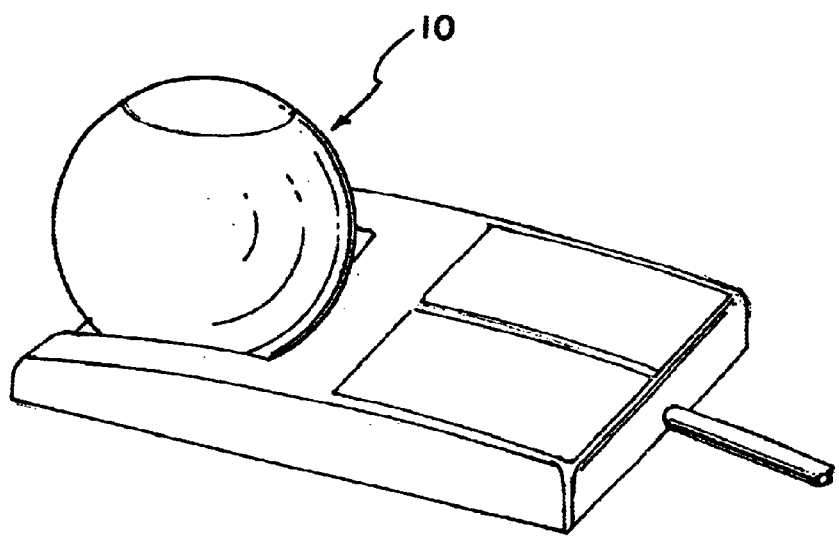
FIG. 5 is an alternative embodiment of the therapeutic device when utilized as a computer mouse.

The therapeutic device 10 may be combined with other functional devices such as a computer mouse as illustrated in FIG. 5.

The device 10 may additionally be refrigerated, or otherwise cooled, so that the device is relatively cool as compared to the body. Cryotherapy is the use of cold temperature to reduce inflamation or otherwise treat the body. Accordingly the device 10 may provide (1) pressure point therapy together with (2) magnetic therapy and/or (3) cryotherapy.

The preferred device 10 has a diameter of about 2 and ½ inches. Additionally, since the device 10 is formed of urethane resin, it can easily be colored in standard colors such as red, blue, yellow, black, or green. Other custom colorations may also be created. Furthermore, other additives as is known in the art of resin casting may be included with the resin such as pecan shavings to give the device 10a "wood" look or feel, or brass shavings to give the device 10a "metal" look, etc.

Numerous alternations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein:

1. A therapeutic device for a portion of a human body comprising:

a solid structure having a continuously curved dome outer top surface to provide a pressure point at a portion of the human body; and a magnet located within a top half of the structure to provide a magnetic field at the pressure point.

2. The therapeutic device of claim 1 wherein the magnet is located within a top quarter of the structure.

3. The therapeutic device of claim 1 wherein the solid structure is initially to a temperature below a human body temperature prior to contact with a human body.

4. The therapeutic device of claim 1 wherein the magnet has a disc shape.

5. The therapeutic device of claim 4 wherein an outer circumference of the magnet is exposed along the outer top surface of the structure.

6. The therapeutic device of claim 1 wherein the curved dome outer top surface is substantially round.

7. The therapeutic device of claim 6 wherein the top surface is ball-shaped.

8. The therapeutic device of claim 1 wherein a bottom surface of the structure is substantially flat.

9. The therapeutic device of claim 1 wherein the solid structure is formed of a cured resin.

10. The therapeutic device of claim 1 wherein the magnet is a ferrite ceramic magnet.

11. The therapeutic device of claim 1 wherein the structure is not deformable.

12. A method of treating a portion of the human body comprising the steps of:

(a) applying a therapeutic device having a continuously curved dome solid outer top surface, and a magnet located within a top half of the therapeutic device to a portion of the body to be treated;

(b) utilizing the continuously curved dome surface to apply a pressure point on the portion of the human body; and (c) allowing the magnet to simultaneously perform magnetic therapy to the portion of the body to be treated.

13. The method of claim 12 further comprising the step of chilling the therapeutic device prior to applying to the portion of the body; and simultaneously providing cyrotherapy to the portion of the body along with magnetic therapy and pressure point treatment.

* * * * *